United States Patent [19]

Cragoe, Jr. et al.

[11] 4,085,211

[45] Apr. 18, 1978

[54] PYRAZINECARBOXAMIDES AND PROCESSES FOR PREPARING SAME

[75] Inventors: Edward J. Cragoe, Jr., Lansdale; Otto W. Woltersdorf, Jr., Chalfont; Charles N. Habecker, Lansdale, all of Pa.

[73] Assignee: Merck & Co., Inc., Rahway, N.J.

[21] Appl. No.: 722,442

[22] Filed: Sep. 13, 1976

Related U.S. Application Data

[63] Continuation-in-part of Ser. No. 640,803, Dec. 15, 1975, abandoned.

[51] Int. Cl.$^2$ .................. A61K 31/495; C07D 295/18
[52] U.S. Cl. ............................. 424/250; 260/268 C; 260/268 H; 260/268 FT; 260/250 BN; 544/120; 544/121

[58] Field of Search ............... 260/250 BN, 247.2 A, 260/268 C, 268 H, 268 FT; 424/250, 248.54 T

[56] References Cited

U.S. PATENT DOCUMENTS

| 3,300,494 | 1/1967 | Cragoe | 260/250 |
|---|---|---|---|
| 3,313,813 | 4/1967 | Cragoe | 260/250 |

Primary Examiner—Donald G. Daus
Assistant Examiner—Jose Tovar
Attorney, Agent, or Firm—Michael C. Sudol, Jr.

[57] ABSTRACT

The case involves novel pyrazinecarboxamides and processes for preparing same. The pyrazinecarboxamides are excellent eukalemic agents possessing diuretic and natriuretic properties.

20 Claims, No Drawings

PYRAZINECARBOXAMIDES AND PROCESSES FOR PREPARING SAME

SUMMARY OF RELATED CASES

This case is a continuation-in-part of U.S. patent application Ser. No. 640,803 filed in the U.S. patent and Trademark Office on Dec. 15, 1975, now abandoned.

BACKGROUND OF THE INVENTION

The background to this invention U.S. Pat. No. 3,313,813 patented Apr. 11, 1967 and issued to Edward J. Cragoe, Jr., shows novel (3-amino-5,6-disubstituted-pyrazinoyl)guanidine compounds. The compounds of the U.S. Pat. No. 3,313,813 are useful because they possess diuretic and natriuretic properties. They differ from most of the known, effective diuretic agents, however, in that the compounds of U.S. Pat. No. 3,313,813 selectively enhance the excretion of sodium ions while simultaneously causing a decrease in excretion of potassium ions. The potassium loss, which is caused by known diuretics, often results in a severe muscular weakness. Since the compounds of the U.S. Pat. No. 3,313,813 prevent the potassium depletion, they have this decided advantage as diuretics. As diuretic agents, they can be used for the treatment of edema, hypertension and other diseases or conditions known to be responsive to this therapy and are especially useful when used in combination with or concomitantly with potassium losing diuretic agents.

Applicants' instant pyrazinecarboxamide compounds shown in Formula I subsequently differ from the compounds shown in U.S. Pat. No. 3,313,813, in that they have a guanylureido group ($-N=C(NH_2)NH-CONH_2$) or substituted guanylureido group in place of the guanidino group of the compounds in the stated U.S. Patent. Applicants have found that the guanylureido group changes the pharmaceutical action and utility of these compounds. It has been found in U.S. Pat. No. 3,313,813 that the pyrazinoylguanidine compounds therein described when co-administered with other diuretic agents known to enhance the elimination of potassium ions along with sodium ions, will maintain the potassium ion excretion at approximately the normal or control rate and thus overcome this undesirable property of other diuretic agents.

In actuality, applicants' compounds in the instant case as further described, accomplish the objective previously achieved by using a combination of the pyrazinoylguanidine compounds of U.S. Pat. No. 3,313,813 with diuretic agents which cause elimination of sodium with concomitant excessive potassium elimination. Thus, the effect of introducing a carboxamide group to the pyrazinoylguanidine compounds of U.S. Pat. No. 3,313,813 results in producing eukalemic saluretic agents. Since the compounds of the instant invention are thus eukalemic saluretic agents they constitute single entities which are useful for the treatment of edema and hypertension and other diseases or conditions known to be responsive to this therapy.

SUMMARY OF THE INVENTION

The instant case covers novel pyrazinecarboxamide compounds and processes for making the same. The novel pyrazinecarboxamides of this invention are depicted in Formula I below.

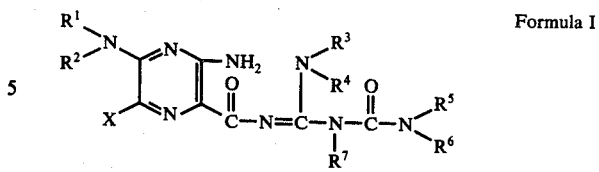

Formula I wherein
$R^1$ is hydrogen, lower alkyl having from 1 to 5 carbon atoms such as methyl, ethyl, isopropyl, n-butyl, n-pentyl, cycloalkyl having from 3 to 6 carbon atoms such as cyclopropyl, cyclopentyl and cyclohexyl; lower alkenyl having from 2 to 3 carbon atoms such as allyl;

$R^2$ is hydrogen, lower alkyl having from 1 to 5 carbon atoms such as methyl, ethyl, isopropyl and n-pentyl, $R^1$ and $R^2$ can be joined to form, with the nitrogen atom to which they are attached, a heterocyclic ring having 3 to 6 carbon atoms therein; and can also be joined to form a heterocyclic ring with the nitrogen atom to which they are attached, said heterocyclic ring having an additional nitrogen atom in addition to the nitrogen atom to which $R^1$ and $R^2$ are attached such as to form a piperazine ring;

$R^3$ is hydrogen, lower alkyl having from 1 to 5 carbon atoms such as methyl, ethyl, isopropyl, butyl and pentyl, cycloalkyl having from 3 to 6 nuclear carbon atoms such as cyclopropyl, cyclopentyl and cyclohexyl;

$R^4$ is hydrogen, lower alkyl having from 1 to 5 carbon atoms such as methyl, ethyl, isopropyl, butyl and n-pentyl; cycloalkyl having from 3 to 6 nuclear carbon atoms such as cyclopropyl, cyclopentyl and cyclohexyl;

$R^3$ and $R^4$ can be joined to form a heterocyclic ring with the nitrogen atom to which they are attached, said ring having 4 to 6 carbon atoms therein;

$R^5$ is hydrogen, lower alkyl having from 1 to 5 carbon atoms such as methyl, ethyl, isopropyl, butyl, secbutyl, isobutyl and pentyl, cycloalkyl having from 3 to 6 nuclear carbon atoms such as cyclopropyl, cyclobutyl, cyclopentyl and cyclohexyl; aryl, particularly phenyl and substituted aryl particularly substituted phenyl wherein the substituent is $C_{1-C5}$ lower alkyl or halo, aralkyl such as benzyl or phenethyl, halolower alkyl ($C_{1-5}$) such as 2,2,2-trifluoroethylamino, loweralkylamino or diloweralkylamino such as dimethylamino, lower alkenyl such as allyl, lower alkynyl such as propargyl, heterocycle such as 2,3 or 4-pyridyl, heterocycleloweralkyl such as furfuryl, loweralkoxycarbonylloweralkyl such as ethoxycarbonylmethyl, carboxyloweralkyl such as carboxymethyl, loweralkoxy such as methoxy, hydroxyloweralkyl such as hydroxyethyl, wherein the lower alkyl in the above groups for $R^5$ where it appears represents from 1-5 carbon atoms;

$R^6$ is hydrogen; lower alkyl having from 1 to 5 carbon atoms such as methyl, ethyl, isopropyl, butyl and pentyl, cycloalkyl having from 3 to 10 nuclear carbon atoms such as cyclopropyl, cyclopentyl, cyclohexyl and adamantyl;

$R^5$ and $R^6$ can be joined to form a heterocyclic ring having from 3 to 6 carbon atoms with the nitrogen atom to which they are attached;

$R^5$ and $R^6$ can also be joined to form a heterocyclic ring with the nitrogen atom to which they are attached, said heterocyclic ring having additional oxygen or nitrogen atoms in addition to the nitrogen atom to which $R^5$ and $R^6$ are attached such as to form a piperidine or a morpholine ring;

$R^7$ is hydrogen, lower alkyl having 1 to 5 carbon atoms such as methyl, ethyl, isopropyl, butyl or n-pentyl;

$R^3$ and $R^7$ can be joined to form an alkylene bridge of from 2 to 3 carbon atoms, thus forming a carbon bridged chain, X is halogen such as chloro, bromo, fluoro or iodo, and the pharmaceutically acceptable non-toxic acid addition salts thereof.

The preferred compounds of this invention, in other words those having enhanced diuretic, saluretic activity while maintaining unchanged potassium blood levels are those compounds of Formula I wherein $R^1$ is hydrogen, $R^2$ is hydrogen, or lower alkyl having from 1 to 3 carbon atoms but particularlly isopropyl, $R^3$ is hydrogen, $R^4$ is hydrogen, or lower alkyl having from 1 to 3 carbon atoms but particularly methyl;

$R^5$ is hydrogen, $R^6$ is hydrogen or lower alkyl having from 1 to 3 carbon atoms but particularly isopropyl or ethyl, $R^7$ is hydrogen, X is chloro, and the pharmaceutically acceptable non-toxic acid addition salts thereof.

Specifically preferred compounds of this invention are as follows:

3,5-diamino-6-chloro-N{[(isopropylaminocarbonyl)amino]aminomethylene}-2-pyrazinecarboxamide;

3,5-diamino-6-chloro-N{[(ethylaminocarbonyl)amino]aminomethylene}-2-pyrazinecarboxamide hydrochloride monohydrate;

3,5-diamino-6-chloro-N{[(ethylaminocarbonyl)amino]-(methylamino)methylene}-2-pyrazinecarboxamide;

3-amino-5-isopropylamino-6-chloro-N-{[(ethylaminocarbonyl)amino](methylamino)methylene}-2-pyrazinecarboxamide;

3,5-diamino-N-{[(aminocarbonyl)amino](methylamino)methylene}-6-chloro-2-pyrazinecarboxamide hydrochloride monohydrate;

3-amino-5-isopropylamino-6-chloro-N-{[(aminocarbonyl)amino]aminomethylene}-2-pyrazinecarboxamide dihydrochloride monohydrate;

3,5-diamino-N-{[(aminocarbonyl)amino]aminomethylene}-6-chloro-2-pyrazinecarboxamide hydrochloride hemihydrate;

3-amino-5-isopropylamino-6-chloro-N{[(ethylaminocarbonyl)amino]aminomethylene}-2-pyrazinecarboxamide.

The compounds of this invention as shown by Formula I and the preferred compounds discussed above are useful because they possess diuretic and natriuretic properties. In addition, they are useful eukalemic saluretics, in other words, the compounds of the instant case cause neither loss or abnormal retention of potassium ions. In contradistinction, the pyrazinoylguanidine compounds of U.S. Pat. No. 3,313,813 do cause a decrease in the excretion of potassium ions. However, other well known diuretics such as furosemide, chlorthalidone and acetazolamide cause an increase in potassium excretion which often results in muscular weakness. Applicants' compounds combine in a single agent the advantages of a combination of the known pyrazinoylguanidine diuretics of U.S. Pat. No. 3,313,813 which decrease potassium with the known diuretics which cause a potassium loss. Thus, the compounds of this invention maintain the excretion of potassium at approximately normal levels while causing an increased renal elimination of sodium ions and water which is the desirable characteristics of the diuretic.

Also covered within the scope of the above Formula I compounds and the preferred compounds are the pharmaceutically acceptable acid addition salts thereof. These salts can be made by reacting the free base with a pharmaceutically acceptable acid such as for example, hydrochloric acid, sulfuric acid, hydrobromic acid or isethionic acid. These salts, as stated above, are to be considered as included in this invention.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like. Several pharmaceutical formulations are prepared as shown in Examples 35 to 37.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds disclosed in this invention in Formula I and the preferred compounds can be formed according to one or more of five processes described below. The first process can be depicted by the following equation:

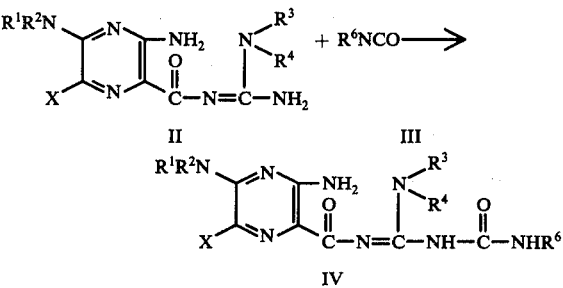

involving a reaction of a pyrazinoylguandine with a subsititued isocyanate to produce the desired product. The reaction is usually run in an inert solvent preferably a solvent such as dimethylformamide or dimethylsulfoxide at a temperature from about room temperature to the reflux temperature of the particular solvent used. The reaction time is usually from one to 48 hours and the reactants are in mole to mole ratios. None of these reaction conditions are critical and they can be varied by those skilled in the art.

A second reaction for forming the end product starts with a N-{[(t-butylaminocarbonyl)amino]aminomethylene}-2-pyrazinecarboxamide (V) particularly the compound formed in Process I if the substituted isocyante used is t-butyl isocyanate. This is depicted in the following equation:

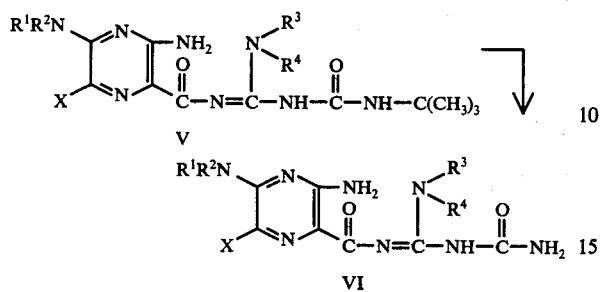

Compound V is pyrolized to form the desired product. Pyrolysis is generally conducted by heating Compound V with concentrated acid such as concentrated HCl to eliminate isobutene. The desired product is then isolated from the reaction mixture by procedures well known in the art.

A third process for preparing the desired products is depicted by the following equation:

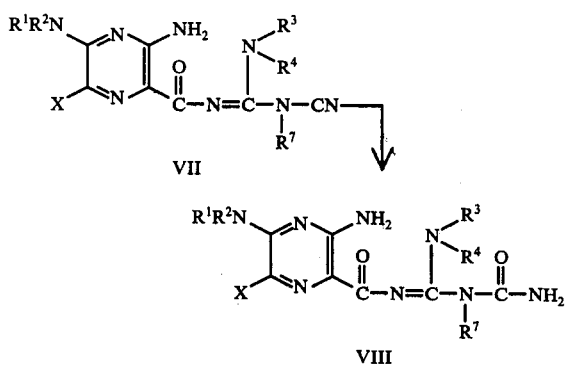

In this reaction scheme, a cyanoguandine is hydrolyzed to the desired amide. The hydrolysis is carried out by reacting the cyanoguandine with concentrated acid such as with concentrated sulfuric acid at a temperature of from about room temperature to 60° and for a time of about 1 to 24 hours. The desired product is then isolated from the reaction mixture by procedures well known in the art.

A fourth process for preparing the desired products of Formula I and the preferred compounds is depicted by the following equation:

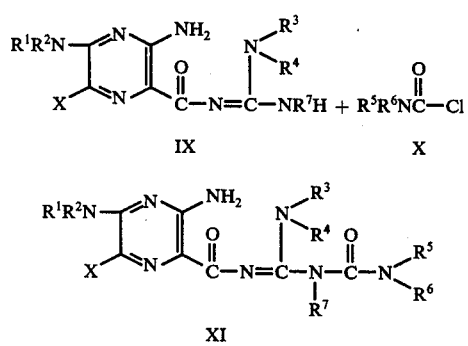

This process involves the reaction of a pyrazinoylguandine with a substituted carbamoyl chloride. The reaction is carried out in an inert solvent such as in pyridine or DMF at a temperature of about room temperature to the reflux temperature of the particular solvent used. 2 to 1 Mole ratio of the reactants IX to X is preferred as IX . HCl is eliminated as a by product.

A fifth process for preparing the desired products of Formula I and the preferred compounds is depicted by the following equation.

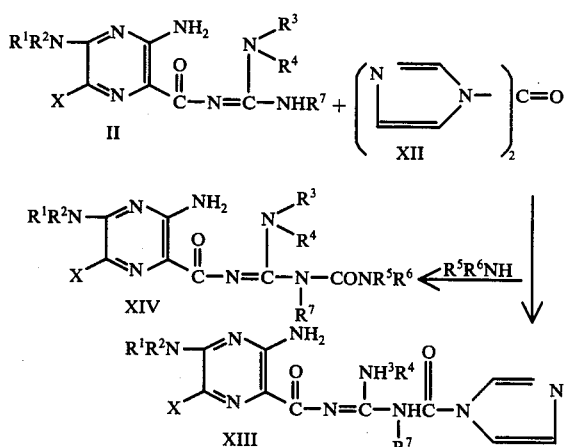

In this reaction scheme wherein $R^1 - R^7$ and X are as previously defined, a pyrazinoylguanidine, II, is reacted with 1,1-carbonyldiimidazole, XII, in an inert solvent such as dimethylsulfoxide, or DMF at a temperature of about room temperature to 100° C. The intermediate synthon XIII may be isolated or treated directly with an amine $R^5R^6NH$ to give the desired product XIV. Where the synthon XIII is isolated, it may be reacted with an amine $R^5R^6NH$ in an inert solvent such as 1-methyl-2-pyrrolidinone or DMF at temperature of about room temperature to 100° C. The desired product can then be isolated by means well known in the art.

All the starting materials used in the five processes described above ae shown in and disclosed in U.s. Pat. No. 3,313,813 mentioned previously or at least can be obviously prepared from compounds disclosed in the aforementioned patent. The preparation of those not shown in U.S. Pat. No. 3,313,813 and which are not obviously prepared therefrom is shown in the Examples.

EXAMPLE 1

Preparation of 3,5-Diamino-6-chloro-N{[(ethylaminocarbonyl)-amino]aminomethylene}-2-pyrazinecarboxamide hydrochloride monohydrate N-Amidino-3,5-diamino-6-chloro-2-pyrazinecarboxamide (9.16 g., 0.04 mole) dissolved in N,N-dimethylformamide (240 ml.) is treated dropwise with ethyl isocyanate (3.16 g., 0.044 mole) over a 10 minute period at 90° C. and heated at 90° C. for 3 hours. The reaction mixture is filtered and poured into water (1 1.) to precipitate 3,5-diamino-6-chloro-N-{[(ethylaminocarbonyl)amino]-aminomethylene}-2-pyrazinecarboxamide. The hydrochloride monohydrate (6.80 g.) is obtained on crystallization from abs. ethanol (800 ml.) and treatment of the hot solution with 12N hydrochloric acid (5 ml.), m.p. 224°–255° C.

Elemental analysis for $C_9H_{13}ClN_8O_2 \cdot HCl \cdot H_2O$; Calc.: C, 30.43; H, 4.54; N, 31.55; Cl, 19.96; Found: C, 30.49; H, 4.59; N, 31.69; Cl, 19.94.

Following the procedure described in Example 1 but using the following amounts of major reactants in place of the corresponding reactants of Example 1, there is obtained the appropriate listed end products.

propylisocyanate (1.87 g., 0.022 mole) over a 10 min. period at 90° C. The solution is heated at 90° C. for 1 hour, filtered and poured into water (150 ml.) to precipitate 3,5-diamino-6-chloro-N-{[(propylaminocarbonyl)amino]aminomethyl-}-2-pyrazinecarboxamide which on recrystallization from n-propanol gives 3.14 g. melting at 220°–221° C.

| Ex. | Pyrazine Carboxamide | Substituted Isocyanate | End product and anaylsis |
|---|---|---|---|
| 2 | N-amidino-3,5-diamino-6-chloro-2-pyrazine-carboxamide (4.58 g., 0.02 mole) | isopropylisocyanate (1.87 g., 0.022 mole) | 3,5-diamino-6-chloro-N-{[(isopropylaminocarbonyl)-amino]aminomethylene}-2-pyrazinecarboxamide hydrochloride monohydrate (1.90 g.) Melting point: 215–218° C. $C_{10}H_{15}ClN_8O_2 \cdot HCl \cdot H_2O$ Calc.: C, 32.53; H, 4.91; N, 30.35; Cl, 19.20; Found: C, 32.31; H, 4.78; N, 29.67; Cl, 19.54. |
| 3 | N-amidino-3,5-diamino-6-chloro-2-pyrazinecarbox-amide (4.58 g., 0.02 mole) | cyclohexylisocyanate (2.76 g., 0.022 mole) | 3,5-diamino-6-chloro-N-{[(cyclohexylaminocarbonyl)-amino]aminomethylene}-2-pyrazinecarboxamide hydrochloride (3.41 g.) Melting point: 225–226° C. $C_{13}H_{19}ClN_8O_2 \cdot HCl$: Calc.: C, 39.91; H, 5.15; N, 28.64; Cl, 18.12; Found: C, 39.64; H, 5.00; N, 28.30; Cl, 18.21. |
| 4 | N-amidino-3,5-diamino-6-chloro-2-pyrazine-carboxamide (9.16 g., (0.04 mole) | methylisocyanate (2.51 g., 0.044 mole) | 3,5-diamino-6-chloro-N-{[(methylaminocarbonyl)-amino]aminomethylene}-2-pyrazinecarboxamide hydrochloride monohydrate (6.71 g.) Melting point: 230–232° C. $C_8H_{11}ClN_8O_2 \cdot HCl \cdot H_2O$: Calc.: C, 28.17; H, 4.14; N, 32.85; Cl, 20.78; Found: C, 28.01; H, 3.86; N, 31.92; Cl, 20.40. |
| 5 | N-amidino-3-amino-5-dimethylamino-6-chloro-2-pyrazinecarboxamide (5.15 g., 0.02 mole) | isopropylisocyanate (1.87 g., 0.022 mole) | 3-amino-5-dimethylamino-6-chloro-N-{[(isopropylaminocarbonyl)amino]aminomethylene}-2-pyrazine-carboxamide hydrochloride (1.14 g.) Melting point: 205–206° C. $C_{12}H_{19}ClN_8O_2 \cdot HCl$: Calc: C, 38.00; H, 5.32; N, 29.55; Found: C, 38.48; H, 5.23; N, 29.21. |
| 6 | N-amidino-3,5-diamino-6-chloro-2-pyrazine-carboxamide (4.58 g., 0.02 mole) | hexylisocyanate (2.80 g., 0.022 mole) | 3,5-diamino-6-chloro-N-{[(hexylaminocarbonyl)-amino]aminomethylene}-2-pyrazinecarboxamide hydrochloride monohydrate (1.35 g.) Melting point: 219–223° C. $C_{13}H_{21}ClN_8O_2 \cdot HCl \cdot H_2O$: Calc.: C, 37.96; H, 5.88; N, 27.24; Found: C, 38.04; H, 5.57; N, 27.39. |
| 6A | N-Amidino-3,5-diamino-6-bromo-2-pyrazine-carboxamide (5.48 g., 0.02 mole) | isopropyl isocyanate (1.8 g., 0.021 mole) | 3,5-diamino-6-bromo-N-{[(isopropylaminocarbonyl)-amino]aminomethylene}-2-pyrazinecarboxamide (2.8 g.) Melting point: 201–3° C. $C_{10}H_{15}BrN_8O_2$; Calc.: C, 33.44; H, 4.21; N, 31.20; Br, 22.25; Found: C, 33.05; H, 4.51; N, 30.52; Br, 21.97. |

EXAMPLE 7

Preparation of 3,5-diamino-6-chloro-N-{[(n-propylaminocarbonyl)amino]aminomethylene}-2-pyrazinecarboxamide N-amidino-3,5-diamino-6-chloro-2-pyrazinecarboxamide (4.58 g., 0.02 mole) dissolved in N,N-dimethylformamide (120 ml.) is treated dropwise with Elemental analysis for $C_{10}H_{15}ClN_8O_2$: Calc.: C, 38.16; H, 4.80; N, 35.60; Cl, 11.26; Found: C, 38.43; H, 5.20; N, 34.75; Cl, 11.26.

Following the procedure of Example 7 but substituting the following amounts of major reactants in place of the corresponding reactants of Example 7 there is obtained the appropriate listed end product

| Ex. | Pyrazine Carboxamide | Substituted Isocyanate | End Product and Analysis |
|---|---|---|---|
| 8 | N-amidino-3,5-diamino-6-chloro-2-pyrazine-carboxamide (4.58 g., 0.02 mole) | m-tolylisocyanate (2.93 g., 0.022 mole) | 3,5-diamino-6-chloro-N-{[(m-toluidinocarbonyl)-amino]aminomethylene}-2-pyrazinecarboxamide (4.68 g.) Melting point: 208–210° C. $C_{14}H_{15}ClN_8O_2$; Calc.: C, 46.35; H 4.17; N, 30.89; Cl, 9.77; Found: C, 46.24; H, 4.23; N, 30.61; Cl, 9.82. |
| 9 | N-amidino-3,5-diamino-6-chloro-2-pyrazine-carboxamide (4.58 g., 0.02 mole) | p-chlorophenyliso-cyanate (3.38 g., 0.022 mole) | 3,5-diamino-6-chloro-N-{[(p-chloroanilino-carbonyl)amino]aminomethylene}-2-pyrazine-carboxamide (2.62 g.) Melting point: 228–231° C. $C_{13}H_{12}Cl_2N_8O_2$: Calc.: C, 40.75; H, 3.16; N, 29.24; Cl, 18.50; Found: C, 40.24; H, 3.11; N, 29.21; Cl, 18.47. |
| 10 | N-amidino-3,5-diamino-6-chloro-2-pyrazine carboxamide (4.58 g., 0.02 mole) | p-tolylisocyanate (2.93 g., 0.022 mole) | 3,5-diamino-6-chloro-N-{[(p-toluidinocarbonyl)-amino]aminomethylene}-2-pyrazinecarboxamide (3.71 g.) Melting point: 221–224° C. $C_{14}H_{15}ClN_8O_2$; Calc.: C, 46.35; N, 4.17; N, 30.89; Found: C, 45.86; H, 4.41; N, 30.72. |
| 11 | N-methylamidino-3,5-di- | ethylisocyanate | 3,5-diamino-6-chloro-N{[(ethylaminocarbonyl)- |

-continued

| Ex. | Pyrazine Carboxamide | Substituted Isocyanate | End Product and Analysis |
|---|---|---|---|
|  | amino-6-chloro-2-pyrazine carboxamide (4.87 g., 0.02 mole) | (1.42 g., 0.022 mole) | amino](methylamino)methylene}-2-pyrazine-carboxamide (4.13 g.) Melting point: 212–213° C. $C_{10}H_{15}ClN_8O_2$: Calc.: C, 38.16; H, 4.80; N, 35.60; Cl, 11.26; Found: C, 37.87; H, 4.94; N, 35.24; Cl, 11.57. |
| 12 | N-methylamidino-3-amino-5-isopropyl-amino-6-chloro-2-pyrazinecarboxamide (10.0 g., 0.035 mole) | ethylisocyanate (2.77 g., 0.0385 mole) | 3-amino-5-isopropylamino-6-chloro-N-{[(ethyl-aminocarbonyl)amino](methylamino)methylene}-2-pyrazinecarboxamide (6.7 g.) Melting point: 147–149° C. $C_{13}H_{21}ClN_8O_2$: Calc.: C, 43.76; H, 5.93; N, 31.40; Found: C, 43.63; H, 6.01; N, 30.83. |
| 13 | N-amidino-3-amino-5-isopropylamino-6-chloro-2-pyrazine carboxamide (5.43 g., 0.02 mole) | isopropyliso-cyanate (1.87 g., 0.022 mole) | 3-amino-5-isopropylamino-6-chloro-N-{[(isopropyl-aminocarbonyl)amino]aminomethylene}-2-pyrazine-carboxamide (3.04 g.) Melting point: 127–132° C. $C_{13}H_{21}ClN_8O_2$: Calc.: C, 43.76; H, 5.93; N, 31.40; Cl, 9.94; Found: C, 43.55; H, 5.89; N, 30.92; Cl, 10.18. |
| 14 | N-amidino-3,5-diamino-6-chloro-2-pyrazine-carboxamide (6.87 g., 0.03 mole) | phenylisocyanate (36 ml., 0.033 mole) | 3,5-diamino-6-chloro-N-{[(anilinocarbonyl)amino]-aminomethylene}-2-pyrazinecarboxamide (8.0 g.) Melting point: 215° C. $C_{13}H_{13}ClN_9O_2$: Calc.: C, 44.77; H, 3.76; N, 32.13; Found: C, 44.82; H, 3.92; N, 31.69. |
| 15 | N-amidino-3-amino-5-isopropylamino-6-chloro-2-pyrazine carboxamide (10.0 g., 0.037 mole) | ethylisocyanate (2.9 g., 0.0387 mole) | 3-amino-5-isopropylamino-6-chloro-N-{[(ethylamino-carbonyl)amino]aminomethylene}-2-pyrazinecarbox-amide (4.2 g.) Melting point: 138–40° C. $C_{12}H_{19}ClN_8O_2$: Calc.: C, 42.04; H, 5.59; Cl, 10.34; Found: C, 42.19; H, 5.76; Cl, 10.09. |
| 16 | N-dimethylamidino-3-amino-5-isopropyl-amino-6-chloro-2-pyrazinecarboxamide (3.57 g., 0.012 mole) | ethylisocyanate (0.94 g., 0.0132 mole) | 3-amino-5-iso-propylamino-6-chloro-N-{[(ethylamino-carbonyl)amino](dimethylamino)methylene}-2-pyrazinecarboxamide Melting point: 167–169° C. $C_{14}H_{23}ClN_8O_2$: Calc.: C, 45.34; H, 6.25; N, 30.22; Cl, 9.56; Found: C, 45.31; H, 6.13; N, 29.52; Cl, 9.75. |
| 17 | N-amidino-3,5-diamino-6-chloro-2-pyrazine-carboxamide (2.29 g., 0.01 mole) | butylisocyanate (1.09 g., 0.011 mole) | 3,5-diamino-N-{[(butylaminocarbonyl)amino]-aminomethylene}-6-chloro-2-pyrazinecarboxamide Melting point: 206–208° C. $C_{11}H_{17}ClN_8O_2$: Calc.: C, 40.19; H, 5.21; N, 34.08; Cl, 10.78; Found: C, 40.43; H, 5.34; N, 33.29; Cl, 10.60. |
| 18 | N-amidino-3,5-diamino-6-chloro-2-pyrazine-carboxamide (6.87 g., 0.03 mole) | p-fluorophenyliso-cyanate (4.54 g., 0.033 mole) | 3,5-diamino-6-chloro-N-{[(p-fluoroanilinocarbonyl)-amino]aminomethylene}-2-pyrazinecarboxamide Melting point: 219–220° C. $C_{13}H_{12}ClN_8O_2$: Calc.: C, 42.58; H, 3.30; N, 30.55; Found: C, 42.51; H, 3.58; N, 30.25. |
| 19 | N-amidino-3,5-diamino-6-chloro-2-pyrazine-carboxamide (6.87 g., 0.03 mole) | o-tolylisocyanate (4.40 g., 0.03 mole) | 3,5-diamino-6-chloro-N-{[ClFN amino]aminomethylene}-2-pyrazinecarboxamide (1.47 g.) Melting point: 202–203° C. $C_{14}H_{15}ClN_8O_2 \cdot \frac{1}{2} H_2O$ Calc.: C, 45.80; H, 4.25; N, 30.53; Cl, 9.65; Found: C, 45.50; H, 4.30; N, 30.62; Cl, 9.58. |

EXAMPLE 20

3-Amino-5-cyclopentylamino-6-chloro-N-{[(ethylaminocarbonyl)amino]methylaminomethylene}-2-pyrazinecarboxamide Step A: N-methylamidino-3-amino-5-cyclopentylamino-6-chloro-2-pyrazinecarboxamide To a solution of methylguanidine in methanol (150 ml.) prepared from methylguanidine sulfate (108.5 g.) and sodium methoxide (40.4 g.) is added methyl 3-amino-5-cyclopentylamino-6-chloropyrazinoate (32.85 g.). The reaction is refluxed for ½ hour then poured into ice water (300 ml.) affording 28.0 g. of N-methylamidino-3-amino-5-cyclopentylamino-6-chloro-2-pyrazinecarboxamide which melts at 184°–187° C. after recrystallization from 2-propanol.

Elemental analysis for $C_{10}H_{18}ClN_7O$: Calc.: C, 46.22; H, 5.81; N, 31.44; Found: C, 46.56; H, 5.65; N, 30.57.

Step B: 3-amino-5-cyclopentylamino-6-chloro-N-{[(ethylaminocarbonyl)amino]methylaminomethylene}-2-pyrazinecarboxamide By following the procedure described in Example 7 using as the reactants N-methylamidino-3-amino-5-cyclopentylamino-6-chloro-2-pyrazinecarboxamide (8.72 g., 0.027 mole), N,N-dimethylformamide (200 ml.) and ethylisocyanate (2.41 g., 0.033 mole) there is obtained 4.0 g. of 3-amino-5-cyclopentylamino-6-chloro-N-{[(ethylaminocarbonyl)-amino]methylaminomethylene}-2-pyrazinecarboxamide which melts at 164° C. after recrystallization from ethanol.

Elemental analysis for $C_{15}H_{23}ClN_8O_2$: Calc.: C, 47.06; H, 6.06; N, 29.27; Found: C, 47.30; H, 6.30; N, 29.00.

EXAMPLE 21

3-Amino-5-dimethylamino-6-chloro-N-{[(ethylaminocarbonyl)-amino]methylaminomethylene}-2-pyrazinecarboxamide Step A: N-Methylamidino-3-amino-5-dimethylamino-6-chloro-2-pyrazinecarboxamide By following the procedure described in Example 20, Step A using as the reactants methylguanidine sulfate (40. g.) methanol (75 ml.), sodium methoxide (16.2 g.) and methyl 3-amino-5-dimethylamino-6-chloropyrazinoate (15.4 g.) there is obtained 15.0 g. of N-methylamidino-3-amino-5-dimethylamino-6-chloro-2-pyrazinecarboxamide which melts at 227° C. without further purification.

Elemental analysis for $C_9H_{14}ClN_7O$: Calc.: C, 39.78; H, 5.19; Cl, 13.05; Found: C, 39.55; H, 5.08; Cl, 13.25.

Step B: 3-Amino-5-dimethylamino-6-chloro-N-{[(ethylaminocarbonyl)amino]methylaminoethylene}-2-pyrazinecarboxamide By following the procedure described in Example 7 using as the reactants N-methylamidino-3-amino-5-dimethylamino-6-chloro-2-pyrazinecarboxamide (15 g.), N,N-dimethylformamide (150 ml.) and ethylisocyanate (4.35 g.) then treating the reaction mixture after ½ hour with water (40 ml.) there is obtained 15.5 g. of 3-amino-5-dimethylamino-6-chloro-N-{[(ethylaminocarbonyl)amino]methylaminomethylene}-2-pyrazinecarboxamide which melts at 157° C.

Elemental analysis for $C_{12}H_{19}ClN_8O_2$: Calc.: C, 42.04; H, 5.59; Cl, 32.69; Found: C, 41.99; H, 5.59; Cl, 32.30.

EXAMPLE 22

3-Amino-5-pyrrolidino-6-chloro-N-{[(ethylaminocarbonyl)amino]methylaminomethylene}-2-pyrazinecarboxamide Step A: N-Methylamidino-3-amino-5-pyrrolidino-6-chloro-2-pyrazinecarboxamide By following the procedure described in Example 21 Step A using as the reactants methylguanidine sulfate (71 g.), sodium methoxide (26.4 g.), methanol (444 ml.) and methyl 3-amino-5-pyrrolidino-6-chloropyrazinoate (21.5 g.) there is obtained 26.2 g. of N-methylamidino-3-amino-5-pyrrolidino-6-chloro-2-pyrazinecarboxamide which melts at 245°-8° C.

Elemental analysis for $C_{11}H_{16}ClN_7O$: Calc.: C, 44.37; H, 5.42; N, 32.93; Found: C, 44.24; H, 5.46; N, 32.23.

Step B: 3-Amino-5-pyrrolidino-6-chloro-N-{[(ethylaminocarbonyl)amino]methylaminomethylene}-2-pyrazinecarboxamide By following the procedure described in Example 7 using as the reactants N-methylamidino-3-amino-5-pyrrolidino-6-chloro-2-pyrazinecarboxamide (8,03 g.), N,N-dimethylformamdide (184 ml.) and ethylisocyanate (2.34 g.) there is obtained 5.0 g. of 3-amino-5-pyrrolidino-6-chloro-N-{[(ethylaminocarbonyl)amino]methylaminomethylene}-2-pyrazinecarboxamide which melts at 197°-200° C. after recrystallization from methanol.

Elemental analysis for $C_{14}H_{21}ClN_8O_2$: Calc.: C, 45.59; H, 5.73; N, 30.38; Found: C, 45.64; H, 5.82; N. 30.00.

EXAMPLE 23

Preparation of 3,5-diamino-N-{[(aminocarbonyl)amino]aminomethylene}-6-chloro-2-pyrazinecarboxamide hydrochloride hemihydrate Step A: 3,5-Diamino-N-{[(tert-butylaminocarbonyl)amino]aminomethylene}-6-chloro-2-pyrazinecarboxamide hemihydrate N-Amidino-3,5-diamino-6-chloro-2-pyrazinecarboxamide (46 g., 0.2 mole) is dissolved in N,N-dimethylformamide (1 l.) at 140° C., cooled to 90° C. then treated dropwise with tert-butyl isocyanate (21.84 g., 0.22 mole) over a ½ hr. period. The solution is heated at 90° C. for 18 hours, filtered and poured into water (2 l.) to precipitate 29.8 g. of 3,5-diamino-N-{[(tert-butylaminocarbonyl)amino]aminomethylene}-6-chloro-2-pyrazinecarboxamide hemihydrate which melts at 206°-207° C. after crystallization from isopropyl alcohol.

Elemental analysis for $C_{11}H_{17}ClN_8O_2 \cdot ½ H_2O$: Calc.: C, 39.14; H, 5.37; N, 33.20; Found: C, 38.93; H, 5.18; N, 33.26.

Step B: 3,5-Diamino-N-{[(aminocarbonyl)amino]aminomethylene}-6-chloro-2-pyrazinecarboxamide hydrochloride hemihydrate 3,5-Diamino-N-{[(tert-butylaminocarbonyl)amino]aminomethylene}-6-chloro-2-pyrazinecarboxamide hemihydrate (29.8 g., 0.091 mole) is added portionwise to warm 12N hydrochloric acid (70 ml.) with stirring. Upon heating at 90° C. the reaction mixture becomes a solution accompanied by vigorous gas evolution. Within 10 minutes a precipitate begins to form. After 40 minutes at 90° C. the solid product is collected and washed with ice-water and ethanol to give 19.6 g. of 3,5-diamino-N-{[(aminocarbonyl)amino]aminomethylene}-6-chloro-2-pyrazinecarboxamide hydrochloride hemihydrate which melts at 245° C.

Elemental analysis for $C_7H_9ClN_8O_2 \cdot HCl \cdot ½ H_2O$: Calc.: C, 26.45; H, 3.48; N, 35.25; Cl, 22.31; Found: C, 26.36; H, 3.28; N, 34.65; Cl, 22.38.

Following the procedure of Example 23, Steps A and B but using the following pyrazinecarboxamides in place of the pyrazinecarboxamide used in Example 23, Step A, but using an equivalent amount of t-butylisocyanate and then following the procedure of Example 23B but using the appropriate pyrazinecarboxamide from Step A of that example the appropriate end product as listed is obtained.

| Ex. | Pyrazine-Carboxamide | Product Step A | Desired Product |
|---|---|---|---|
| 24 | N-amidino-3-amino-5-dimethylamino-6-chloro-2-pyrazinecarboxamide (10.95 g., 0.04 mole) | 3-amino-5-dimethylamino-6-chloro N-{[(t-butylaminocarbonyl)amino]-aminomethylene}-2-pyrazine carboxamide. (8.95 g.) Melting point: 163-167° C. $C_{13}H_{21}ClN_8O_2$: Calc.: C, 43.76; H, 5.93; N, 31.40; Cl, 9.94; Found: C, 43.07; H, 5.78; N, 31.59; Cl, 10.18. | 3-amino-5-dimethylamino-N-{[(aminocarbonyl)amino]aminomethylene}-6-chloro-2-pyrazinecarboxamide hydrochloride hemihydrate (5.1 g.) Melting point: 249-253° C. $C_9H_{13}ClN_8O_2 \cdot HCl \cdot ½ H_2O$: Calc.: C, 31.22; H, 4.37; N, 32.37; Cl, 20.48; Found: C, 31.57; H, 4.25; N, 31.85; Cl, 20.46. |
| 25 | N-methylamidino-3,5-diamino-6-chloro-2- | 3,5-diamino-6-chloro-N-{[(tert-butylaminocarbonyl)amino](methyl- | 3,5-diamino-N-{[(aminocarbonyl)amino]-(methylamino)methylene}-6-chloro- |

-continued

| Ex. | Pyrazine-Carboxamide | Product Step A | Desired Product |
|---|---|---|---|
|  | pyrazinecarboxamide (9.74 g., 0.04 mole) | amino)methylene}-2-pyrazine-carboxamide (10.91 g.) Melting point: 198–200° C. $C_{12}H_{19}ClN_8O_2$: Calc.: C, 42.05; H, 5.59; N, 32.69; Found: C, 41.32; H, 5.61; N, 32.96. | 2-pyrazinecarboxamide hydrochloride monohydrate (7.91 g.) Melting point: 190–192° C. $C_8H_{11}ClN_8O_2 \cdot HCl \cdot H_2O$: Calc.: C, 28.17; H, 4.14; N, 32.85; Cl, 20.78; Found: C, 28.81; H, 4.17; N, 33.09; Cl, 20.71. |
| 26 | N-methylamidino-3-amino-5-isopropyl-amino-6-chloro-2-pyrazinecarboxamide (8.58 g., 0.03 mole) | 3-amino-5-isopropylamino-6-chloro-N-{[(tert-butylamino-carbonyl)amino](methylamino)-methylene}-2-pyrazinecarbox-amide (4.68 g.) Melting point: 157–160° C. $C_{15}H_{25}ClN_8O_2$: Calc.: C, 46.81; H, 6.55; Cl, 9.21; Found: C, 47.07; H, 6.75; Cl, 9.49. | 3-amino-5-isopropylamino-6-chloro-N-{[(aminocarbonyl)amino](methylamino)-methylene}-2-pyrazinecarboxamide dihydrochloride monohydrate (3.85 g.) Melting point: 222–224° C. $C_{11}H_{17}ClN_8O_2 \cdot 2HCl \cdot H_2O$: Calc.: C, 31.48; H, 5.04; N, 26.70; Cl, 25.34; Found: C, 31.40; H, 4.98; N, 26.22; Cl, 25.55. |
| 27 | N-amidino-3-amino-5-(N-methyl-N-propyl)-amino-6-chloro-2-pyrazinecarboxamide (20.5 g., 0.072 mole) | 3-amino-5-(N-methyl-N-propyl)-amino-6-chloro-N-{[(tert-butyl-aminocarbonyl)amino]amino-methylene}-2-pyrazinecarboxamide Melting point: 165–8° C. | 3-amino-5-{N-methyl-N-propyl)amino-6-chloro-N-{[(aminocarbonyl)amino]-aminomethylene}-2-pyrazinecarboxamide hydrochloride monohydrate Melting point: 198–202° C. $C_{11}H_{17}ClN_8O_2 \cdot HCl \cdot H_2O$: Calc.: C, 34.47; H, 5.26; N, 29.24; Cl, 18.50; Found: C, 34.46; H, 5.06; N, 29.09; Cl, 18.24. |
| 28 | N-amidino-3-amino-5-isopropylamino-6-chloro-2-pyrazine carboxamide (4.9 g., 0.018 mole) | 3-amino-5-isopropylamino-6-chloro-N-{[(tert-butylamino-carbonyl)amino]aminomethylene}-2-pyrazinecarboxamide (2.6 g.) Melting point: 157–62° C. | 3-amino-5-isopropylamino-6-chloro-N-{[(aminocarbonyl)amino]aminomethylene}-2-pyrazinecarboxamide hydrochloride Melting point: 210–13° C. $C_{10}H_{15}ClN_8O_2 \cdot HCl$: Calc.: C, 34.20; H, 4.59; N, 31.91; Found: C, 33.88; H, 4.61; N, 31.03. |

EXAMPLE 29

Preparation of 3,5-diamino-N-{[(aminocarbonyl)amino]aminomethylene}-6-chloro-2-pyrazinecarboxamide hydrobromide 3,5-Diamino-N-{[(tert-butylaminocarbonyl)amino]-aminomethylene}-6-chloro-2-pyrazinecarboxamide hemihydrate (10.0 g., 0.03 mole) is heated with 48% hydrobromic acid at 90° C. for ½ hr. to precipitate a yellow product which is collected and washed with ice-water and ethanol affording 8.06 g. of 3,5-diamino-N-{[(aminocarbonyl)amino]aminomethylene}-6-chloro-2-pyrazinecarboxamide hydrobromide melting at 232°–235° C.

Elemental analysis for $C_7H_9ClN_8O_2 \cdot HBr$: Calc.: C, 23.78; H, 2.85; N, 31.70; Found: C, 23.88; H, 3.00; N, 32.00.

EXAMPLE 30

Preparation of 3,5-diamino-N-{[(aminocarbonyl)amino]aminomethylene}-6-chloro-2-pyrazinecarboxamide hemisulfate monohydrate Step A: 3,5-diamino-6-chloro-N-(cyanamidino)-2-pyrazinecarboxamide Cyanoguanidine (33.6 g., 0.4 mole) is added to a suspension of sodium hydride (16.0 g., 0.4 mole) in N,N-dimethylformamide (250 ml.) and stirring is continued at 25° C. for ½ hr. The mixture is cooled to <10° C., methyl 3,5-dimaino-6-chloro-2-pyrazinoate (20.26 g., 0.1 mole) is added, and the mixture is stirred at 25° C. for 18 hrs., then poured into water (600 ml.). The aqueous layer is extracted with ether and acidified with glacial acetic acid (75 ml.) to precipitate 20.0 g. of 3,5-diamino-6-chloro-N-(cyanamidino)-2-pyrazinecarboxamide, m.p. >300° C. on reprecipitation from dimethylformamide: water, 1:1.

Elemental analysis for $C_7H_7N_8O$: Calc.: C, 33.01; H, 2.77; N, 44.01; Found: C, 33.39; H, 2.60; N, 43.74.

Step B: 3,5-Diamino-N-{[(aminocarbonyl)amino]-aminomethylene}-6-chloro-2-pyrazinecarboxamide hemisulfate monohydrate 3,5-Diamino-6-chloro-N-(cyanamidino)-2-pyrazinecarboxamide (200 mg., 1 m.mole) is added to 36N sulfuric acid with stirring at 25° C. After 18 hrs. the solution is added dropwise to crushed ice to precipitate 193 mg. of 3,5-diamino-N-{[(aminocarbonyl)amino]-aminomethylene}-6-chloro-2-pyrazinecarboxamide hemisulfate monohydrate.

Elemental analysis for $C_7H_9ClN_8O_2 \cdot \frac{1}{2} H_2SO_4 \cdot H_2O$: Calc.; C, 24.75; H, 3.56; N, 32.99; Cl, 10.44; Found: C, 24.78; H, 3.21; N, 32.70; Cl, 10.29.

EXAMPLE 31

Preparation of 3,5-Diamino-6-chloro-N-{[(4-methylpiperazinocarbonyl)amino]aminomethylene}-2-pyrazinecarboxamide N-Amidino-3,5-diamino-6-chloro-2-pyrazinecarboxamide (13.74 g., 0.06 mole), 1-methyl-4-piperazinecarbonylchloride hydrochloride (4.28 g., 0.022 mole) and pyridine (200 ml.) are heated at 90° C. for ½ hr., cooled to 25° C, the solid precipitate filtered off and the filtrate treated with water (500 ml.) to precipitate 3.06 g. of 3,5-diamino-6-chloro-N-{[(4-methylpiperazinocarbonyl)amino]aminomethylene}-2-pyrazinecarboxamide which melts at 247°–249° C. after recrystallization from ethanol.

Elemental analysis for $C_{12}H_{18}ClN_9O_2$: Calc.: C, 40.51; H, 5.10; N, 35.43; Cl, 9.96; Found: C, 40.61; H, 4.94; N, 35.42; Cl, 10.16.

Following the procedure of Example 31 but using an equivalent amount of all reactants and solvents except substituting the following carbonyl chloride reactant in place of 1-methyl-4-piperazine carbonyl chloride hydrochloride of Example 31 there are prepared the following end products:

EXAMPLE 35

Step A:
3,5-Diamino-6-chloro-N-{[(1-imidazolcarbonyl)amino]-aminomethylene}-2-pyrazinecarboxamide

| | | |
|---|---|---|
| 32 | morpholine carbonyl chloride (3.29 g., 0.022 mole) | 3,5-diamino-6-chloro-N-{[(morpholinocarbonyl)amino]aminomethylene}-2-pyrazinecarboxamide hemihydrate (1.57 g.) Melting point: 248–250° C. $C_{11}H_{15}ClN_8O_2 \cdot \tfrac{1}{2}H_2O$: Calc.: C, 37.56; H, 4.58; N, 31.86; Cl, 10.08; Found: C, 37.94; H, 4.40; N, 31.79; Cl, 10.12. |
| 33 | dimethylcarbamoyl chloride (1.0 ml.) | 3,5-diamino-6-chloro-N-{[(dimethylaminocarbonyl)amino]aminomethylene}-2-pyrazinecarboxamide (1.3 g.) Melting point: 238° C. $C_{10}H_{13}ClN_8O_2$: Calc.: C, 35.95; H, 4.36; Cl, 11.79; Found: C, 35.75; H, 4.16; Cl, 11.76. |

EXAMPLE 34

1-Dimethylaminocarbonyl-2-(3,5-diamino-6-chloro-2-pyrazinecarbonylimino)-imidazolidine hydrochloride Step A: 2-(3,5-Diamino-6-chloro-2-pyrazinecarboxamido)-2-imidazoline To a solution of sodium isopropoxide prepared from sodium (1.3 g., 0.056 gr. at.) in isopropanol (200 ml.) is added 2-aminoimidazoline-mono-p-toluenesulfonate (18.4 g.). The reaction is refluxed for ½ hour then N-tert-butyl-3-(3,5-diamino-6-chloropyrazinecarbonyloxy)-crotonamide (9.8 g.) is added. After one hour at reflux the reaction mixture is filtered and the filter cake slurried in water (200 ml.). On filtering there is obtained 2.3 g. of 2-(3,5-diamino-6-chloro-2-pyrazinecarbonylimino)-imidazolidine which melts at 236° C. and is used in the next step without further purification.

Step B: 1-Dimethylaminocarbonyl-2-(3,5-diamino-6-chloro-2-pyrazinecarbonylimino)-imidazolidine hydrochloride By following the procedure described in Example 31 using as the reactants 2-(3,5-diamino-6-chloro-2-pyrazinecarbonylimino)-imidazolidine (2.3 g.), pyridine (50 ml.) and dimethylcarbamoyl chloride (0.9 ml.) there is obtained 1-dimethylaminocarbonyl-2-(3,5-diamino-6-chloro-2-pyrazinecarbonylimino)-imidazolidine hydrochloride which melts at 168°–70° C. after crystallization from ethanol.

Elemental analysis for $C_{11}H_{15}ClN_8O_2 \cdot HCl$ Calc.: C, 36.37; H, 4.44; N, 30.85; Found: C, 36.65; H, 4.36; N, 30.53.

To a stirred solution of N-amidino-3,5-diamino-6-chloro-2-pyrazinecarboxamide (16.1 g., 0.07 mole) in dimethylsulfoxide (120 ml.) is added 1,1'-carbonyldiimidazole (11.4 g., 0.07 mole). The product which separates is filtered, rinsed with dimethylsulfoxide, water and dried to give 23 g. (93%) of 3,5-diamino-6-chloro-N-{[(1-imidazolcarbonyl)amino]aminomethylene}-2-pyrazinecarboxamide which melts at 250° C. (dec.).

Elemental analysis for $C_{10}H_{10}ClN_9O_2$: Calc.: C, 37.10; H, 3.11; N, 38.95; Cl, 10.95; Found: C, 37.27; H, 3.23; N, 38.40; Cl, 10.80.

Step B: 3,5-Diamino-6-chloro-N-{[(benzyl-aminocarbonyl)amino]aminomethylene}-2-pyrazinecarboxamide To a stirred suspension of 3,5-diamino-6-chloroN-{[(imidazolcarbonyl)amino]aminomethylene}-2-pyrazinecarboxamide (3.2 g., 0.01 mole) in 1-methyl-2-pyrrolidone (30 ml.) is added benzylamine (1.2 ml., 0.017 mole). The reaction mixture is heated on a steam bath for ¾ hour, during which time the solution become clear. The solution is filtered, cooled and treated with water (20 ml.) to precipitate 3,5-diamino-6-chloro-N-{[(benzylaminocarbonyl)amino]aminomethylene}-2-pyrazinecarboxamide which melts at 135° C after recrystallization from ethanol.

Elemental analysis for $C_{14}H_{15}ClN_8O_2$: Calc.: C, 46.35; H, 4.17; Cl, 9.77; Found: C, 46.16; H, 4.32; Cl, 9.95.

Following the procedure of Example 35, Step B, but using the listed amounts of 3,5-diamino-6-chloro-N-{[(imidazolcarbonyl)amino]aminomethylene}-2-pyrazinecarboxamide and the listed amine in place of the amine used in Example 35, Step B, the appropriate end product as listed is obtained.

| Ex. | Amt. of 3,5-diamino-6-chloro-N-{[(imidazolyl-carbonyl)amino]amino-methylene}-2-pyrazine-carboxamide | Amine | End Product |
|---|---|---|---|
| 36 | 3,5-Diamino-6-chloro-N-{[(imidazolcarbonyl)amino]-aminomethylene}-2-pyrazine-carboxamide (3.2 g., 0.01 mole) | cyclopropylamine (1.1 ml.) | 3,5-diamino-6-chloro-N-{[(cyclopropylaminocarbonyl)-amino]aminomethylene}-2-pyrazinecarboxamide (2.0 g.) Melting point; 218° C. $C_{10}H_{13}ClN_8O_2$; Calc.: C, 38.41; H, 4.19; N, 35.83; Found: C, 38.57; H, 4.38; N, 35.59. |
| 37 | 3,5-Diamino-6-chloro-N-{[(imidazolcarbonyl)amino]-aminomethylene}-2-pyrazine carboxamide (3.2 g. 0.01 mole) | 1,1-dimethyl-hydrazine (1.0 ml.) | 3,5-diamino-6-chloro-N-[{[(dimethylamino)aminocarbonyl]-amino}aminomethylene]-2-pyrazinecarboxamide hemihydrate. (1.3 g.) Melting point: 122° C. $C_9H_{14}ClN_9O_2 \cdot \tfrac{1}{2}H_2O$: Calc.: C, 33.28; H, 4.66; Cl, 10.92; Found: C, 33.32; H, 4.90; Cl, 10.97. |
| 38 | 3,5-Diamino-6-chloro-N-{[(imidazolcarbonyl)amino]- | 1,1,1-trifluoro-ethylamine | 3,5-diamino-6-chloro-N-[{[(1,1,1-trifluoroethyl)amino-carbonyl]amino}aminomethylene]-2-pyrazinecarboxamide. |

-continued

| Ex. | Amt. of 3,5-diamino-6-chloro-N-{[(imidazolyl-carbonyl)amino]amino-methylene}-2-pyrazine-carboxamide | Amine | End Product |
|---|---|---|---|
| | aminomethylene}-2-pyrazine carboxamide (3.2 g., 0.01 mole) | hydrochloride (1.5 g., 0.011 mole) triethylamine (1.5 ml. 0.011 mole) | (1.3 g.) Melting point: 236° C. $C_9H_{10}ClF_3N_8O_2$: Calc., C, 30.48; H, 2.84; N, 31.59; Found: C, 30.68; H, 3.00; N, 31.52. |
| 39 | 3,5-Diamino-6-chloro-N-{[(imidazolcarbonyl)-amino]aminomethylene}-2-pyrazinecarboxamide 1.6 g. (0.005 mole) | glycine ethyl ester hydrochloride (0.8 g.) triethylamine (0.75 ml.) | 3,5-diamino-6-chloro-N-{[[(ethoxycarbonyl)methyl-aminocarbonyl]amino}aminomethylene]-2-pyrazine carboxamide (1.1 g.) Melting Point: 219–20° C. $C_{11}H_{15}ClN_8O_4$: Calc.: C, 36.83; H, 4.21; Found: C, 37.24; H, 4.48. |
| 40 | 3.5 g. (0.011 mole) | cyclopentylamine 1.03 g. (0.012 mole) | 3,5-diamino-6-chloro-N-{[(cyclopentylaminocarbonyl)-amino]aminomethylene}-2-pyrazinecarboxamide (2.1 g (57%)) Melting Point: 213–215° dec. $C_{12}H_{17}ClN_8O_2$: Calc.: C, 42.29; H, 5.03; N, 32.88; Cl, 10.40; Found: C, 42.38; H, 5.44; N, 32.25; Cl, 10.45. |
| 41 | 3.2 g. (0.01 mole) | Furfurylamine 1.2 g. (0.012 mole) | 3,5-diamino-6-chloro-N-{[(furfurylaminocarbonyl)-amino]aminomethylene}-2-pyrazinecarboxamide (1.7 g., 49%) Melting Point: 199–201° dec. $C_{12}H_{13}ClN_8O_3$: Calc.: C, 40.86; H, 3.71; N, 31.77; Found: C, 40.54; H, 3.70; N, 31.44. |
| 42 | 3.2 g. (0.01 mole) | propargylamine hydrochloride 1.1 g (0.012 mole) triethylamine 1.25 g (0.012 mole) | 3,5-diamino-6-chloro-N{[(propargylaminocarbonyl)-amino]aminomethylene}-2-pyrazinecarboxamide (1.6 g., 52%) Melting Point: 193–198° dec. $C_{10}H_{11}ClN_8O_2$: Calc.: C, 38.66; H, 3.57; N, 36.07; Found: C, 38.36; H, 3.60; N, 35.98. |
| 43 | 3.2 g. (0.01 mole) | cyclopropylmethyl-amine hydrochloride 1.3 g (0.012 mole) triethylamine 1.25 g (0.012 mole) | 3,5-diamino-6-chloro-N-{[(cyclopropylmethylamino-carbonyl)amino]aminomethylene}-2-pyrazinecarboxamide. (1.0 g., 31%) Melting Point: 210–212° dec. $C_{11}H_{15}ClN_8O_2$: Calc.: C, 40.42; H, 4.63; N, 34.30; Found: C, 40.30; H, 4.57; N, 33.83. |
| 44 | 3.2 g. (0.01 mole) | cyclobutylamine hydrochloride 1.3 g (0.012 mole) triethylamine 1.25 g (0.012 mole) | 3,5-diamino-6-chloro-N{[(cyclobutylaminocarbonyl)-amino]aminomethylene}-2-pyrazinecarboxamide (1.1 g., 34%) Melting Point: 219–221° dec. $C_{11}H_{15}ClN_8O_2$: Calc.: C, 40.43; H, 4.63; N, 34.30; Found: C, 40.74; H, 4.90; N, 33.98. |
| 45 | 3.2 g. (0.01 mole) | methoxyamine hydro-chloride 1.0 g. (0.012 mole) triethylamine 1.25 g (0.012 mole) | 3,5-diamino-6-chloro-N{[(methoxyaminocarbonyl)amino]-aminomethylene}-2-pyrazine carboxamide (1.5 g., 50%) Melting Point: 220° dec. $C_8H_{11}ClN_8O_3$: Calc.: C, 31.74; H, 3.66; N, 37.02; Cl, 11.71; Found: C, 32.43; H, 3.82; N, 37.14; Cl, 11.50. |
| 46 | 3.2 g (0.01 mole) | 2-adamantamine hydro-chloride 2.06 g. (0.011 mole) triethylamine 1.5 ml. (0.011 mole) | 3,5-diamino-6-chloro-N-{[(2-adamantaminocarbonyl)-amino]aminomethylene}-2-pyrazinecarboxamide acetate (600 mg. from ACOH) Melting Point: 129–33° C. $C_{19}H_{27}ClN_8O_4 \cdot C_2H_4O_2$: Calc.: C, 48.87; H, 5.83; N, 24.00; Found: C, 48.52; H, 5.88; N, 24.00 |
| 47 | 3.2 g. (0.01 mole) | 4-aminopyridine 1.04 g. (0.011 mole) | 3,5-diamino-6-chloro-N-{[(4-pyridylaminocarbonyl)amino]-aminomethylene}-2-pyrazinecarboxamide. (370 mg.) Melting Point: 230–2° C. $C_{12}H_{12}ClN_9O_2$: Calc.: C, 41.21; H, 3.46; N, 36.04; Cl, 10.14 Found: C, 40.24; H, 3.77; N, 36.19; Cl, 10.50. |
| 48 | 3.24 g. (0.01 mole) | 2-aminomethyl-4-tert-butyl-6-iodo-phenol hydrochloride 3.76 g (0.011 mole) Triethylamine 1.5 ml. (0.011 mole) | 3,5-diamino-6-chloro-N-{[[(2-hydroxy-3-iodo-5-tert-butyl)-benzylaminocarbonyl]amino}aminomethylene]-2-pyrazine-carboxamide-N-methyl-2-pyrrolidinone solvate (2.87 g.) Melting Point: 171–3° C. $C_{18}H_{22}ClIN_8O_3 \cdot C_5H_9NO$: Calc.: C, 41.86; H, 4.73; Cl, 5.37 Found: C, 42.10; H, 4.85; Cl, 5.38. |
| 49 | 3.2 g (0.01 mole) | allylamine 630 mg (0.011 mole) DMF (instead of 1-methyl-2-pyrol-lidinone) 30 ml. | 3,5-diamino--6-chloro-N-{[(allylaminocarbonyl)amino]-aminomethylene}-2-pyrazinecarboxamide (910 mg.) Melting Point: 203–4° C. $C_{10}H_{13}ClN_8O_2$: Calc.: C, 38.41; H, 4.19; Cl. 11.34; Found: C, 38.11; H, 4.27; Cl. 11.45. |
| 50 | 1.6 g. (0.005 mole) | NH$_4$OH 1 ml. (0.015 mole) | 3,5-diamino-6-chloro-N[(aminocarbonyl)amino]amino-methylene}-2-pyrazinecarboxamide (710 mg.) Melting Point: ~300° C. $C_7H_9ClN_8O_2$: Calc.: C, 30.84; H, 3.33; Cl, 13.00; Found: C, 30.53; H, 3.60; Cl, 13.11. |
| 51 | 3.2 g. (0.01 mole) | 1-methylpropyl-amine 1.2 ml. | 3,5-diamino-6-chloro-N{[(1-methylpropylaminocarbonyl)-amino aminomethylene}-2-pyrazinecarboxamide hemihydrate. (2.0 g.) |

-continued

| Ex. | Amt. of 3,5-diamino-6-chloro-N-{[(imidazolyl-carbonyl)amino]amino-methylene}-2-pyrazine-carboxamide | Amine | End Product |
|---|---|---|---|
| 52 | 3.2 g. (0.1 mole) | 2-methylpropyl-amine 1.2 ml. | Melting point: 192° $C_{11}H_{17}ClN_8O_2(+\frac{1}{2}H_2O)$: Calc.: C, 39.11; H, 5.37; N, 33.18; Cl, 10.50; Found: C, 39.61; H. 5.05; N, 33.61; Cl, 10.33. 3,5-diamino-6-chloro-N-{[(2-methylpropylaminocarbonyl)-amino]aminomethylene}-2-pyrazinecarboxamide. (2.0 g.) Melting point: 212° C. $C_{11}H_{17}ClN_8O_2$: Calc.: C, 40.18; H, 5.21; N, 34.08; Found: C, 40.28; H, 5.34; N, 33.79. |
| 53 | 1.62 g. (0.005 mole) | 1-adamantamine 0.83 g. (0.0055 mole) N-methyl-2-pyrroli-done 20 ml. | 3,5-diamino-6-chloro-N-{[(1-adamantylaminocarbonyl)amino]-aminomethylene}-2-pyrazinecarboxamide hemisesquihydrate (215 mg., 10%) Melting point: 147–52° C. $C_{17}H_{23}ClN_8O_2 \cdot \frac{3}{4}H_2O$: Calc.: C, 48.58; H, 5.87; N, 26.66; Found: C, 48.60; H, 5.93; N, 26.71. |
| 54 | 3.2 g. (0.01 mole) | ethanolamine 1.5 ml. | 3,5-diamino-6-chloro-N-{[(2-hydroxyethylaminocarbonyl)-amino]aminomethylene}-2-pyrazinecarboxamide (2.5 g.) Melting point: 209° C. $C_9H_{13}ClN_8O_3$: Calc.: C, 34.13; H, 4.14; N, 35.38; Found: C, 34.23; H, 4.56; N, 35.16. |

EXAMPLE 55

3,5-Diamino-6-fluoro-N-{[(isopropylaminocarbonyl-)amino]-aminomethylene}-2-pyrazinecarboxamide Step A: Methyl 3,5-diamino-6-fluoropyrazinoate In a reactor cooled to −78° C. in an acetone-dry ice bath is placed methyl 3,5-diaminopyrazinoate (6 g.) and liquid hydrogen fluoride (70 ml.). A stream of fluorinehelium mixture (1:4 ᵛ/v) is passed through the solution for 5½ hours at <78° C. followed by a vigorous stream of nitrogen to remove the solvent. The reaction residue is treated with conc. hydrochloric acid (60 ml.) evaporated to dryness, dissolved in water (75 ml.) and neutralized with aqueous sodium hydroxide to give methyl 3,5-diamino-6-fluoropyrazinoate (5 g.) which is purified by sublimation (140°–50° C, 0.05 mm Hg) and recrystalliation from 2-propanol.

Elemental analysis for $C_6H_7FN_4O_2$: Calc.: C, 38.71; H, 3.79; N, 30.10; F, 10.21; Found: C, 38.49; H, 3.58; N, 29.96; F, 10.45.

Step B: N-Amidino-3,5-diamino-6-fluoro-2-pyrazinecarboxamide

To a stirred solution of sodium methoxide (1.45 g.) in methanol (25 ml.) is added guanidine hydrochloride (3.0 g.). After ¼ hour, the sodium chloride which separates is filtered, the guanidine solution distilled to 6 ml., treated with the methyl 3,5-diamino-6-fluoropyrazinoate (960 mg.) and heated on a steam bath for five minutes. Trituration of the reaction with water provides N-amidino-3,5-diamino-6-fluoro-2-pyrazinecarboxamide (600 mg.) which melts at 233° C. after reprecipitation from aqueous hydrochloric acid with aqueous sodium hydroxide.

Elemental analysis for $C_6H_8FN_7O$: Calc.: C, 33.80; H, 3.78; F, 8.91; Found: C, 33.97; H, 3.91; F, 9.18.

Step C: 3,5-Diamino-6-fluoro-N-{[(1-imidazolcarbonyl)amino]aminomethylene}-2-pyrazinecarboxamide To a stirred solution of N-amidino-3,5-diamino-6-fluoro-2-pyrazinecarboxamide (3.0 g.) in dimethylsulfoxide (30 ml.) is added 1,1-carbonyldiimidazole (2.3 g.). The reaction is stirred for ½ hour during which time 3,5-diamino-6-fluoro-N-{[(1-imidazolcarbonyl)amino]-aminomethylene}-2-pyrazinecarboxamide separates; then is filtered, rinsed with dimethylsulfoxide, water and acetone. M.P. 227°–30° C.

Elemental analysis for $C_{10}H_{10}FN_9O_2$: Calc.: C, 39.09; H, 2.38; N, 41.03; Found: C, 39.18; H, 3.32; N, 40.14.

EXAMPLE 56

3,5-Diamino-6-fluoro-N-{[(isopropylaminocarbonyl-)amino]aminomethylene}-2-pyrazinecarboxamide Following the procedure of Example 54, Step B but substituting 3,5-diamino-6-fluoro-N-{[(imidazolcarbonyl)amino]aminomethylene}-2-pyrazinecarboxamide (1.3 g.) and isopropylamine (0.45 ml) in place of the corresponding reactants in Example 54, Step B there is obtained 3,5-diamino-6-fluoro-N-{[(isopropylaminocarbonyl)amino]aminomethylene}-2-pyrazinecarboxamide. Yield: 600 Mg. M.P. 221° C.

Elemental analysis for $C_{10}H_{15}FN_8O_2$: Calc. C, 40.27; H, 5.07; N, 37.57; Found: C, 39.98; H, 5.07; N, 37.14.

EXAMPLE 57

Preparation of 3-Amino-5-isopropylamino-6-chloro-N-{[(ethylaminocarbonyl)amino]aminomethylene}-2-pyrazinecarboxamide Step A: 3-Amino-5-isopropylamine-6-chloro-N-{[(1-imidazolcarbonyl)amino]aminomethylene}-2-pyrazinecarboxamide A solution of N-amidino-3-amino-5-isopropylamino-6-chloro-2-pyrazinecarboxamide (42 g., 0.154 mole) in dimethylsulfoxide (300 ml.) is treaed with carbonyldiimidazole (25 g., 0.154 mole) and stirred for ½ hour at 25° C. The reaction mixture is treated with ice water (500 ml.) and the 3-amino-5-isopropylamino-6-chloro-N-{[(1-imidazolcarbonyl)amino]aminomethylene}-2-pyrazinecarboxamide which separates is filtered, rinsed with water, isopropanol and dried. M.P. 191° C.

Step B: 3-Amino-5-isopropylamino-6-chloro-N-{[(ethylaminocarbonyl)amino]aminomethylene}-2-pyrazinecarboxamide A mixture of 3-amino-5-isopropylamino-6-chloro-N-{[(1-imidazolcarbonyl)amino]aminomethylene}-2-pyrazinecarboxamide (18.25 g., 0.05 mole) and ethylamine (2.7 g., 0.06 m) in 1-methyl-2-pyrrolidinone (150 ml.) is heated at 95° for ½ hour, filtered and the filtrate slowly diluted with water (350 ml.) to precipitate 3-amino-5-isopropylamino-6-chloro-N-{[(ethylaminocarbonyl)amino]aminomethylen}-2-pyrazinecarboxamide which melts at 148°–150° C.

Elemental analysis for $C_{12}H_{19}ClN_8O_2$: Calc.: C, 42.04; H, 5.59; N, 32.69; Found: C, 41.83; H, 5.71; N, 32.59.

Following the procedure of Example 57, Step B, but substituting the following amounts of major reactors in place of the corresponding reactants in Example 57, Step B there is obtained the appropriate listed end product.

| Ex. | Pyrazinecarboxamide | Amine | End Product |
|---|---|---|---|
| 58 | 3-amino-5-isopropylamine-6-chloro-N-{[(imidazol-carbonyl)amino]amino-methylene}-2-pyrazine-carboxamide. 3.66 g., 0.01 mole | isopropylamine 0.708 g., 0.012 mole | 3-amino-5-isopropylamino-6-chloro-N-{[(isopropyl-aminocarbonyl)amino]aminomethylene}-2-pyrazine carboxamide. Melting point: 127–132° C. |
| 59 | 3,5-diamino-6-chloro-N-{[(imidazolcarbonyl)-amino]aminomethylene}-2-pyrazinecarboxamide 3.2 g., 0.01 mole | ethylamine 0.54 g., 0.012 mole | 3,5-diamino-6-chloro-N-{[(ethylaminocarbonyl)-amino]aminomethylene}-2-pyrazinecarboxamide hydrochloride monohydrate. Melting point: 224–225° C. |
| 60 | 3,5-diamino-6-chloro-N-{[(imidazolcarbonyl)-amino]aminomethylene}-2-pyrazinecarboxamide 3.2 g., 0.01 mole | isopropylamine 0.708 g., 0.012 mole | 3,5-diamino-6-chloro-N-{[(isopropylaminocarbonyl)-amino]aminomethylene}-2-pyrazinecarboxamide hydrochloride monohydrate Melting point: 215–218° C. |
| 61 | 3,5-diamino-6-chloro-N{[(imidazolcarbonyl)-amino]aminomethylene}-2-pyrazinecarboxamide 3.2 g., 0.01 mole | n-propylamine 0.708 g., 0.012 mole | 3,5-diamino-6-chloro-N-{[(n-propylaminocarbonyl)-amino]aminomethylene}-2-pyrazinecarboxamide Melting point: 220–221° C. |

EXAMPLE 61-A 3,5-Diamino-6-chloro-N-{[(carboxymethylaminocarbonyl)amino]aminomethylene}-2-pyrazinecarboxamide dihydrochloride hydrate Step A: 3,5-Diamino-6-chloro-N-{[(tert-butoxycarbonylmethylaminocarbonyl)amino]aminomethylene}-2-pyrazinecarboxamine hemihydrate A mixture of 3,5-diamino-6-chloro-N-{[(imidazolincarbonyl)amino]aminomethylene}-2-pyrazinecarboxamide (4.8 g., 0.015 mole), glycine-tert. butyl ester hydrochloride (2.9 g.), triethylamine (2.25 ml.) and 1-methyl-2-pyrrolidinone (120 ml.), is heated at 95° C. for ½ hour, filtered and treated with ice (140 g.) to precipitate 5.2 g. of 3,5-diamino-6-chloro-N-{[(tert-butoxycarbonylmethylaminocarbonyl)amino]aminomethylene}-2-pyrazinecarboxamide hemihydrate.

Elemental analysis for $C_{13}H_{19}ClN_8O_4 \cdot \frac{1}{2} H_2O$: Calc.: C, 39.44; H, 5.09; N, 28.31; Found: C, 29.19; H, 5.09; N, 28.05.

Step B: 3,5-Diamino-6-chloro-N-{[(carboxymethylaminocarbonyl)amino]aminomethylene}-2-pyrazinecarboxamide dihydrochloride hydrate Concentrated hydrochloric acid (100 ml) and 3,5-diamino-6-chloro-N-{[(tert-butoxycarbonylmethylaminocarbonyl)amino]aminomethylene}-2-pyrazinecarboxamide hemihydrate (2 g.) are united in a 500 ml. round bottomed flask and heated with stirring on a steam bath for 10 minutes during which time the evolution of isobutylene is observed. The hot reaction mixture is filtered. The 3,5-diamino-6-chloro-N{[(carboxymethylaminocarbonyl)amino]aminomethylene}-2-pyrazinecarboxamide dihydrochloride hydrate which is collected and dried in a steam cabinet melts at 252° C (dec.).

Elemental analysis for $C_9H_{11}ClN_8O_4 \cdot 2HCl \cdot H_2O$: Calc.: C, 25.64; H, 3.59; N, 26.58; Cl, 25.22; Found: C, 25.92; H, 3.87; N, 26.39; Cl, 25.20.

EXAMPLE 62

Compressed Tablet containing 50 mg. of active ingredient.

| | Per tablet, Mg. |
|---|---|
| 3,5-Diamino-6-chloro-N{[ethylaminocarbonyl)-amino]aminomethylene}-2-pyrazinecarboxamide hydrochloride monohydrate | 50 |
| Calcium phosphate dibasic | 200 |
| Ethyl cellulose (as 5% solution in ethanol) | 5 |
| Unmixed granulation | 255 |
| Add: | |
| Starch, corn | 14 |
| Magnesium stearate | 1 |
| | 270 |

Directions: Mix the active ingredient above and calcium phosphate and reduce to a No. 60 mesh powder. Granulate with Ethocel in alcohol and pass the wet granulation through a No. 10 screen. Dry the granulation at 110° F. for 12–18 hours. Dry grind to a No. 20 mesh. Incorporate the "adds" and compress into tablets each weighing 270 mg.

EXAMPLE 63

Dry filled capsule containing 50 mg. of active ingredient.

| | Per capsule, mg. |
|---|---|
| 3,5-diamino-6-chloro-N-{[(isopropyl-aminocarbonyl)amino]aminomethylene}-2-pyrazinecarboxamide hydrochloride monohydrate | 50 |
| Lactose | 273 |
| Magnesium stearate | 2 |
| Mixed powders | 325 |

Mix the active ingredient above, lactose, and magnesium stearate and reduce to a No. 60 mesh powder. Encapsulate, filling 325 mg. in each No. 2 capsule.

The above formulations can be employed to prepare compressed tablets or capsules or other novel compounds of this invention hereinbefore described.

EXAMPLE 64

Combination dosage form in dry filled capsule.

| | Per capsule, Mg. |
|---|---|
| 3-amino-5-isopropylamino-6-chloro-N- | |

| | Per capsule, Mg. |
|---|---|
| {[(ethylaminocarbonyl)amino]-aminomethylene}-2-pyrazinecarboxamide | 50 |
| Magnesium stearate | 2 |
| Lactose | 223 |
| Mixed powders | 275 |

Mix all of the above ingredients, reduce to a No. 60 mesh powder and encapsulate, filling 275 mg. in each No. 2 capsule.

The above examples describe the preparation of certain compounds which are illustrative of the novel compounds of this invention, and certain specific dosage forms suitable for administering the novel compounds, it is to be understood that the invention is not to be limited to the specific compounds described in the examples or by the specific reaction conditions described for the preparation of these compounds or by the specific ingredients included in the pharmaceutical preparations, but is to be understood to embrace variations and modifications thereof which fall within the scope of the appended claims.

What is claimed is:

1. A compound of the formula:

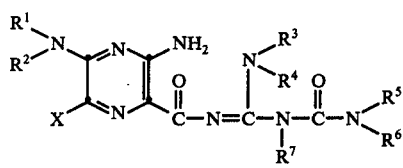

wherein
$R^1$ is hydrogen, lower alkyl having from 1 to 5 carbon atoms cycloalkyl having from 3 to 6 carbon atoms, lower alkenyl having from 2 to 3 carbon atoms;
$R^2$ is hydrogen, lower alkyl having 1 to 5 carbon atoms;
$R^1$ and $R^2$ are joined to form with the nitrogen atom to which they are attached a pyrrolidine or piperazine ring;
$R^3$ is hydrogen, lower alkyl having from 1 to 5 carbon atoms; cycloalkyl having from 3 to 6 nuclear carbon atoms;
$R^4$ is hydrogen, lower alkyl having from 1 to 5 carbon atoms; cycloalkyl having from 3 to 6 nuclear carbon atoms;
$R^5$ is hydrogen, lower alkyl having 1 to 5 carbon atoms; cycloalkyl having from 3 to 6 nuclear carbon atoms; phenyl or substituted phenyl wherein the substituent is lower alkyl or halo; benzyl or phenethyl; trifluoroethyl, lower alkylamino, diloweralkylamino, allyl, propargyl, pyridyl, furfuryl, methoxy or hydroxy ethyl; ethoxy carbonyl methyl or carboxy methyl;
$R^6$ is hydrogen, lower alkyl having from 1 to 5 carbon atoms; cycloalkyl having from 3 to 10 nuclear carbon atoms;
$R^5$ and $R^6$ are joined to form a piperazine or morpholine ring with the nitrogen atom to which they are attached;
$R^7$ is hydrogen, lower alkyl having 1 to 5 carbon atoms;
$R^3$ and $R^7$ are joined to form an alkylene bridge of 2 carbon atoms;

X is halogen; and the pharmaceutically acceptable non-toxic acid addition salts thereof.

2. A compound of the formula:

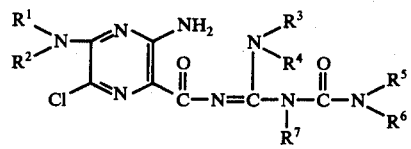

wherein
$R^1$, $R^3$, $R^5$ and $R^7$ are hydrogen;
$R^2$ is hydrogen or lower alkyl having from 1 to 3 carbon atoms;
$R^4$ and $R^6$ are hydrogen or lower alkyl having from 1 to 3 carbon atoms; and the pharmaceutically acceptable non-toxic acid addition salts thereof.

3. A compound of claim 2 wherein
$R^1$, $R^3$, $R^5$ and $R^7$ are hydrogen;
$R^2$ is isopropyl;
$R^4$ is methyl;
$R^6$ is ethyl; which is 3-amino-5-isopropylamino-6-chloro-N-{[(ethylaminocarbonyl)amino](methylamino)methylene}-2-pyrazinecarboxamide.

4. A compound of claim 2 wherein $R^1$, $R^2$, $R^3$, $R^4$, $R^5$, $R^6$, and $R^7$ are hydrogen which is 3,5-diamino-N-{[(aminocarbonyl)amino]aminomethylene}-6-chloro-2-pyrazinecarboxamide.

5. A compound of claim 2 wherein
$R^1$, $R^2$, $R^3$, $R^5$, $R^6$ and $R^7$ are hydrogen; and
$R^4$ is methyl; which is 3,5-diamino-N-{[(aminocarbonyl)amino](methylamino)methylene}-6-chloro-2-pyrazinecarboxamide.

6. A compound of claim 2 wherein
$R^1$, $R^3$, $R^5$, $R^6$ and $R^7$ are hydrogen;
$R^2$ is isopropyl; and
$R^4$ is methyl; which is 3-amino-5-isopropylamino-6-chloro-N-{[(aminocarbonyl)amino](methylamino)methylene}-2-pyrazinecarboxamide.

7. A compound of claim 2 wherein
$R^1$, $R^2$, $R^3$, $R^4$, $R^5$ and $R^7$ are hydrogen; and
$R^6$ is ethyl; which is 3,5-diamino-6-chloro-N{[(ethylaminocarbonyl)amino]aminomethylene}-2-pyrazinecarboxamide hydrochloride monohydrate.

8. A compound of claim 2 wherein
$R^1$, $R^2$, $R^3$, $R^5$ and $R^7$ are hydrogen;
$R^4$ is methyl; and
$R^6$ is ethyl; which is 3,5-diamino-6-chloro-N{[(ethylaminocarbonyl)amino](methylamino)methylene}-2-pyrazinecarboxamide.

9. A compound of claim 2 wherein
$R^1$, $R^2$, $R^3$, $R^4$, $R^5$ and $R^7$ are all hydrogen; and
$R^6$ is isopropyl; which is 3,5-diamino-6-chloro-N-{[(isopropylaminocarbonyl)-amino]aminomethylene}-2-pyrazinecarboxamide hydrochloride monohydrate.

10. A compound of claim 2 wherein
$R^1$, $R^3$, $R^4$, $R^5$ and $R^7$ are hydrogen; and
$R^2$ and $R^6$ are isopropyl; which is 3-amino-5-isoproylamino-6-chloro-N-{(isopropylaminocarbonyl)amino]aminomethylene}-2-pyrazinecarboxamide.

11. A compound of claim 2 wherein
$R^1$, $R^2$, $R^3$, $R^4$, $R^5$ and $R^7$ are hydrogen; and
$R^6$ is tert-butyl: which is 3,5-diamino-N-{[tert-butylaminocarbonyl)amino]-aminomethylene}-6-chloro-2-pyrazinecarboxamide hemihydrate.

12. A compound of claim 2 wherein
R¹, R³, R⁴, R⁵ and R⁷ are hydrogen;
R² is isopropyl; and
R⁶ is ethyl; which is 31-amino-5-isopropylamino-6-chloro-N-{[(ethylaminocarbonyl)amino]aminomethylene}-2-pyrazinecarboxamide.

13. A method of treating edema and/or hypertension which comprises administering to a patient a pharmacologically acceptable does of a compound of the formula:

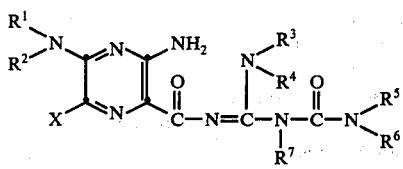

wherein
R¹ is hydrogen, lower alkyl having from 1 to 5 carbon atoms cycloalkyl having from 3 to 6 carbon atoms, lower alkenyl having from 2 to 3 carbon atoms;
R² is hydrogen, lower alkyl having 1 to 5 carbon atoms;
R¹ and R² are joined to form with the nitrogen atom to which they are attached a pyrrolidine or piperazine ring;
R³ is hydrogen, lower alkyl having from 1 to 5 carbon atoms; cycloalkyl having from 3 to 6 nuclear carbon atoms;
R⁴ is hydrogen, lower alkyl having from 1 to 5 carbon atoms; cycloalkyl having from 3 to 6 nuclear carbon atoms;
R⁵ is hydrogen, lower alkyl having 1 to 5 carbon atoms; cycloalkyl having from 3 to 6 nuclear carbon atoms; phenyl or substituted phenyl wherein the substituent is lower alkyl or halo; benzyl or phenethyl; trifluoroethyl, lower alkylamino, diloweralkylamino, allyl, propargyl, pyridyl, furfuryl, methoxy or hydroxy ethyl; ethoxy carbonyl methyl or carboxy methyl;
R⁶ is hydrogen, lower alkyl having from 1 to 5 carbon atoms; cycloalkyl having from 3 to 10 nuclear carbon atoms;
R⁵ and R⁶ are joined to form a piperazine or morpholine ring with the nitrogen atom to which they are attached;
R⁷ is hydrogen, lower alkyl having 1 to 5 carbon atoms;
R³ and R⁷ are joined to form an alkylene bridge of 2 carbon atoms;
X is halogen; and the pharmaceutically acceptable non-toxic acid addition salts thereof.

14. A method of treating edema and hypertension which consists essentially of administering to a patient in need of such treatment a unit dosage of from 5 mg. to 1 gm./day of a compound of the formula:

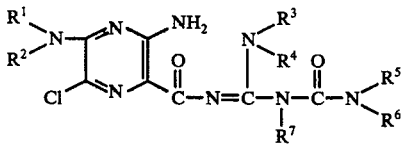

wherein
R¹ is hydrogen;
R² is hydrogen or lower alkyl having from 1 to 3 carbon atoms;
R³ is hydrogen;
R⁴ is hydrogen or lower alkyl having from 1 to 3 carbon atoms;
R⁵ is hydrogen;
R⁶ is hydrogen or lower alkyl having from 1 to 3 carbon atoms;
R⁷ is hydrogen; and the pharmaceutically acceptable non-toxic and addition salts thereof.

15. A method of treatment according to claim 14 wherein the compound to be administered is 3.5-diamino-6-chloro-N-{[(isopropylaminocarbonyl)amino]aminomethylene}-2-pyrazinecarboxamide hydrochloride monohydrate.

16. A method of treatment according to claim 14 wherein the compound to be administered is 3-amino-5-isopropylamino-6-chloro-N-{[(ethylaminocarbonyl)amino]-aminomethylene}-2-pyrazinecarboxamide.

17. A pharmaceutical composition consisting essentially of an active ingredient of a compound of the formula:

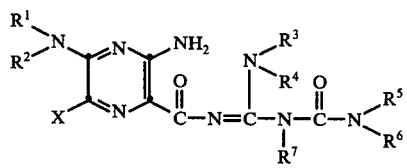

wherein
R¹ is hydrogen, lower alkyl having from 1 to 5 carbon atoms cycloalkyl having from 3 to 6 carbon atoms, lower alkenyl having from 2 to 3 carbon atoms;
R² is hydrogen, lower alkyl having 1 to 5 carbon atoms;
R¹ and R² are joined to form with the nitrogen atom to which they are attached a pyrrolidine or piperazine ring;
R³ is hydrogen, lower alkyl having from 1 to 5 carbon atoms; cycloalkyl having from 3 to 6 nuclear carbon atoms;
R⁴ is hydrogen, lower alkyl having from 1 to 5 carbon atoms; cycloalkyl having from 3 to 6 nuclear carbon atoms;
R⁵ is hydrogen, lower alkyl having 1 to 5 carbon atoms; cycloalkyl having from 3 to 6 nuclear carbon atoms; phenyl or substituted phenyl wherein the substituent is lower alkyl or halo; benzyl or phenethyl; trifluoroethyl, lower alkylamino, diloweralkylamino, allyl, propargyl, pyridyl, furfuryl, methoxy or hydroxy ethyl; ethoxy carbonyl methyl or carboxy methyl;
R⁶ is hydrogen, lower alkyl having from 1 to 5 carbon atoms; cycloalkyl having from 3 to 10 nuclear carbon atoms;
R⁵ and R⁶ are joined to form a piperazine or morpholine ring with the nitrogen atom to which they are attached;
R⁷ is hydrogen, lower alkyl having 1 to 5 carbon atoms;
R³ and R⁷ are joined to form an alkylene bridge of 2 carbon atoms;
X is halogen; and the pharmaceutically acceptable non-toxic acid addition salts thereof.

18. A pharmaceutical composition consisting essentially of an active ingredient of a compound of the formula:

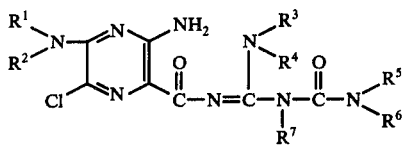

wherein
$R^1$ is hydrogen;
$R^2$ is hydrogen or lower alkyl having from 1 to 3 carbon atoms;
$R^3$ is hydrogen;
$R^4$ is hydrogen or lower alkyl having from 1 to 3 carbon atoms;
$R^5$ is hydrogen;
$R^6$ is hydrogen or lower alkyl having from 1 to 3 carbon atoms;
$R^7$ is hydrogen, and the pharmaceutically acceptable non-toxic acid addition salts thereof and a pharmaceutically acceptable carrier.

19. A pharmaceutical composition according to claim 18 wherein the active ingredient is 3,5-diamino-6-chloro-N [(isopropylaminocarbonyl)amino]-aminomethylene-2-pyrazinecarboxamide hydrochloride monohydrate.

20. A pharmaceutical composition according to claim 18 wherein the active ingredient is 3-amino-5-isopropylamino-6-chloro-N-{[(ethylaminocarbonyl)amino]-aminomethylene}-2-pyrazinecarboxamide.

* * * * *

UNITED STATES PATENT AND TRADEMARK OFFICE
CERTIFICATE OF CORRECTION

PATENT NO. : 4,085,211

DATED : April 18, 1978

INVENTOR(S) : Edward J. Cragoe, Jr., Otto W. Woltersdorf, Jr. and Charles N. Habecker It is certified that error appears in the above-identified patent and that said Letters Patent are hereby corrected as shown below:

Col. 25, line 4, "31" should read -- 3-- .

Col. 26, line 12, "3.5" should read -- 3,5 -- .

Signed and Sealed this

Twenty-sixth Day of September 1978

[SEAL]

Attest:

RUTH C. MASON
Attesting Officer

DONALD W. BANNER
Commissioner of Patents and Trademarks